(12) United States Patent
Sambandam (10) Patent No.: US 10,363,040 B2
(45) Date of Patent: Jul. 30, 2019

(54) ANASTOMOSIS DEVICES

(71) Applicant: W. L. Gore & Associates, Inc., Newark, DE (US)

(72) Inventor: Sakthi Sambandam, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 480 days.

(21) Appl. No.: 14/701,338

(22) Filed: Apr. 30, 2015

(65) Prior Publication Data

US 2015/0313597 A1 Nov. 5, 2015

Related U.S. Application Data

(60) Provisional application No. 61/987,954, filed on May 2, 2014.

(51) Int. Cl.
*A61B 17/11* (2006.01)
*A61B 17/00* (2006.01)
(Continued)

(52) U.S. Cl.
CPC ...... *A61B 17/1114* (2013.01); *A61B 17/0057* (2013.01); *A61B 17/11* (2013.01); *A61F 2/06* (2013.01); *A61F 2/90* (2013.01); *A61B 17/064* (2013.01); *A61B 17/08* (2013.01); *A61B 17/083* (2013.01); *A61B 2017/0641* (2013.01); *A61B 2017/1103* (2013.01); *A61B 2017/1107* (2013.01); *A61B 2017/1132* (2013.01); *A61B 2017/1135* (2013.01); *A61B 2017/1139* (2013.01); *A61F 2002/077* (2013.01)

(58) Field of Classification Search
CPC . A61B 17/0057; A61B 17/11; A61B 17/1114; A61B 17/1128; A61B 17/1146; A61B 2017/00575; A61B 2017/00597; A61B 2017/00606; A61B 2017/00637; A61B 2017/00641; A61B 2017/00676; A61B 2017/1107; A61B 2017/1117; A61B 2017/1132; A61B 2017/1135; A61B 2017/1139; A61B 2017/1142
See application file for complete search history.

(56) References Cited

U.S. PATENT DOCUMENTS 5,741,297 A * 4/1998 Simon ............... A61B 17/0057
604/285
6,616,675 B1 9/2003 Evard
(Continued)

FOREIGN PATENT DOCUMENTS

WO WO-2007100970 A2 9/2007
WO WO-2012034108 A1 3/2012

OTHER PUBLICATIONS

International Search Report, PCT/US2015/028715, dated Aug. 25, 2015, 5 pages.

*Primary Examiner* — Todd J Scherbel (57) ABSTRACT

Implantable medical devices for connecting tissue layers, such as for connecting a gallbladder and a portion of a gastrointestinal tract to create an anastomosis, include a tubular structure having a plurality of apposition portions, a central region, and a covering material. The devices are endoscopically deployable and may include flange members having hinge members or variable properties such as length, angle, shape, material stiffness, and wire diameter.

25 Claims, 6 Drawing Sheets

(51) Int. Cl.
*A61F 2/06* (2013.01)
*A61F 2/90* (2013.01)
*A61B 17/08* (2006.01)
*A61B 17/064* (2006.01)
*A61F 2/07* (2013.01)

(56) References Cited

U.S. PATENT DOCUMENTS

| | | | |
|---|---|---|---|
| 2005/0049675 A1* | 3/2005 | Wallace | A61B 17/11 623/1.13 |
| 2005/0070957 A1* | 3/2005 | Das | A61B 17/0057 606/213 |
| 2007/0244518 A1* | 10/2007 | Callaghan | A61B 17/0057 606/215 |
| 2008/0243151 A1 | 10/2008 | Binmoeller | |
| 2010/0106171 A1 | 4/2010 | Arepally et al. | |
| 2010/0268316 A1* | 10/2010 | Brenneman | A61B 17/083 623/1.11 |
| 2011/0118765 A1 | 5/2011 | Aguirre | |
| 2012/0065652 A1 | 3/2012 | Cully et al. | |
| 2014/0074155 A1 | 3/2014 | Rothstein | |

\* cited by examiner

ANASTOMOSIS DEVICES

FIELD

This present disclosure relates generally to implantable medical devices, and more specifically, to implantable devices for connecting tissue layers to create an anastomosis.

BACKGROUND

An anastomosis is a cross-connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

One aspect of the invention relates to an implantable medical device that includes (1) a barrel portion including a rigid frame having a first end and a second end, (2) a first flange portion including a plurality of first flange members having a first length and a plurality of second flange members having a second length where the first length is less than the second length, (3) a first hinge member including a cover material and flexibly coupling the first end of the barrel portion and the first flange portion, (4) a second flange portion including a plurality of the first flange members and a plurality of the second flange members, and (5) a second hinge member including the cover material. The second hinge member flexibly couples the second end of the barrel portion and the second flange portion. The first flange member may have a geometry and/or a stiffness that is different from that of the second flange member. In exemplary embodiments, the first flange member extends radially from the first and second hinge members at an angle less than 80 degrees and the second flange members extend radially from the first and second hinge members at an angle less than 90 degrees. In some embodiments, the first flange portion provides a first apposition force that is different from a second apposition force provided by the second flange portion. Additionally, at least a portion of the first flange portion and at least a portion of the second flange portion may be covered with a cover material.

A second aspect of the invention relates to an implantable medical device that includes (1) a barrel portion that includes a rigid frame having a first end and a second end, (2) a first flange portion that includes a plurality of first flange members having a first length and a plurality of second flange members having a second length, (3) a first hinge member that includes a cover material and flexibly couples the first end of the barrel portion and the first flange portion, (4) a second flange portion that includes a plurality of third flange members having a third length and a plurality of fourth flange members having a fourth length. The second hinge member includes the cover material and flexibly couples the second end of the barrel portion and the second flange portion. Additionally, in exemplary embodiments, the first length is less than the second length and the third length is less than the fourth length. Further, at least one of the first length and the second length is different from at least one of the third length and the fourth length. In some embodiments, the first flange members extend radially from the first and second hinge members at an angle less than 80 degrees and the second flange members extend radially from the first and second hinge members at an angle less than 90 degrees. In some embodiments, the first and second flange members include a first elongate member having a first geometry and the third and fourth flange members include a second elongate member having a second geometry that is different than the first geometry. In at least one embodiment, the first elongate member has a first stiffness and the second elongate member has a second stiffness that is different than the first stiffness. Additionally, in some embodiments, the first flange member provides a first apposition force, the second flange member provides a second apposition force, the third flange member provides a third apposition force, and the fourth flange member provides a fourth apposition force. Each of the first, second, third, and fourth apposition forces may be different.

A third aspect of the invention relates to an implantable medical device that includes (1) a barrel portion that includes a rigid frame having a first end and a second end, (2) a first flange portion that includes a plurality of first flange members having a first projecting angle and a plurality of second flange members having a second projecting angle that is different than the first projecting angle, (3) a first hinge member that includes a cover material and flexibly couples the first end of the barrel portion and the first flange portion, (4) a second flange portion that includes a plurality of first flange members having the first projecting angle and a plurality of second flange members having the second projecting angle, and (5) a second hinge member that includes the cover material and flexibly couples the second end of the barrel portion and the second flange portion. In at least one exemplary embodiment, the first projecting angle is between about 5 degrees and 80 degrees and the second projecting angle is between about 10 degrees and 90 degrees. The first flange member has a first length and the second flange member has a second length. In some embodiments, the first length is less than the second length. In some other embodiments, the first flange member includes a first elongate member having a first geometry and the second flange member includes a second elongate member having a second geometry that is different than the first geometry. Additionally, the first elongate member may have a stiffness that is different from the stiffness of the second elongate member. In at least one embodiment, the barrel portion includes an elongate member having a first stiffness and the first and second flange portions each include one or more elongate members having a second stiffness that is different than the first stiffness. In a further embodiment, the first flange portion provides a first apposition force and the second flange portion provides a second apposition force that is different than the first apposition force. Further, the first flange member provides a third apposition force and the second flange member provides a fourth apposition force that is different than the third apposition force.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present invention is directed to implantable devices for connecting tissue layers, for example, to circumvent a conduit or organ blockage, such as by creating a direct passage between tissue structures (e.g. connecting a gallbladder and a portion of a gastrointestinal tract) to create an anastomosis that facilitates material flow therebetween. The devices described herein may be endoscopically deployable or deliverable via a catheter and may include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein are configured to be removable after implantation. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. The devices described herein can provide alternative treatments for patients who are not suitable candidates for other types of treatments (e.g., gallbladder removal surgery) and/or to avoid known complications of other types of treatments (e.g., external biliary drainage).

The present disclosure refers to anastomosis devices in an exemplary fashion. That is, it should be understood that the inventive concepts disclosed in this document can also be applied to other types of devices. For example, this disclosure also provides implantable devices that, in some embodiments, can be used for occluding tissue structures, organs, body conduits, blood vessels, the GI tract, and the like. For example, in some embodiments the devices provided herein can be used to occlude septal defects. In some embodiments, the devices provided herein can be used to occlude a patient's vasculature or GI tract. In some such embodiments, the device does not include a tunnel through the device. Rather, in some embodiments a covering material seals the device to inhibit, modulate, or substantially prevent material from flowing through the device.

Figure 1:
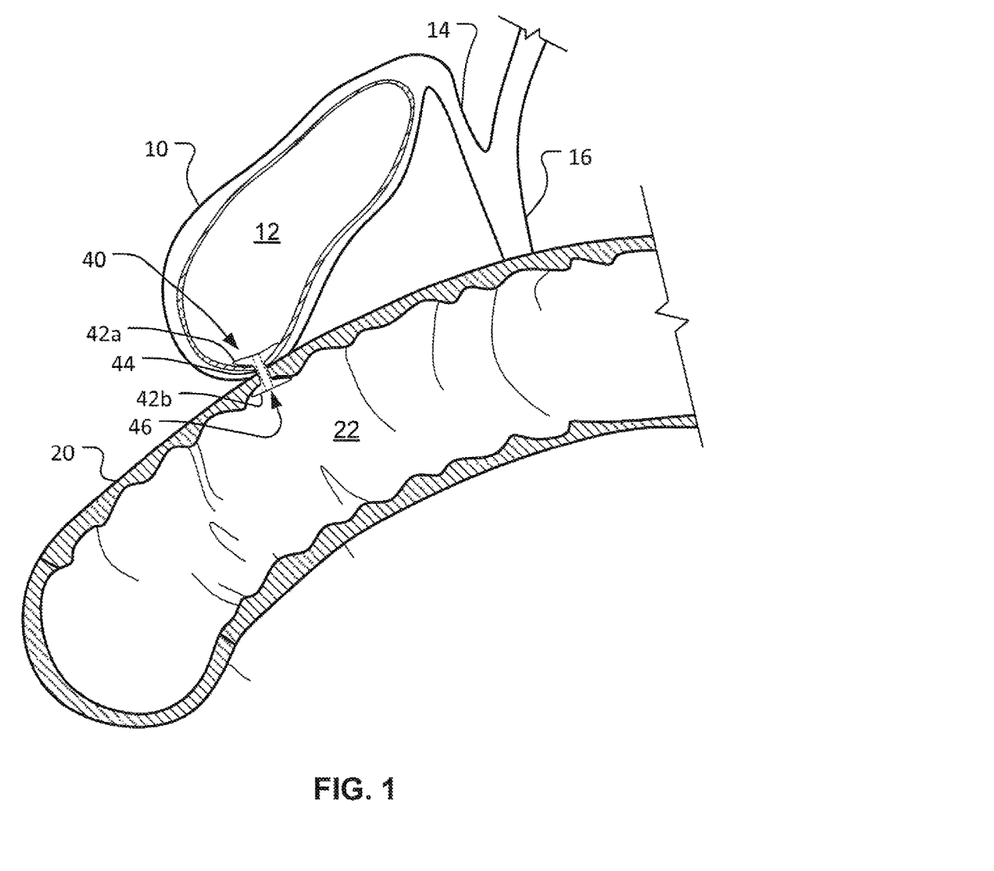
FIG. 1 is a cutaway perspective view of an exemplary anastomosis device that has been implanted within a patient to be a shunt between the patient's gallbladder and intestine in accordance with some embodiments.

Referring to FIG. 1, an exemplary anastomosis device 40 in accordance with some embodiments provided herein can be implanted in a patient to create a fluidic connection between two organs, spaces, tissue structures, conduits, and the like, and combinations thereof. For example, in the depicted implementation the anastomosis device 40 is connecting a gall bladder 10 (that defines an internal gall bladder space 12) with an intestine 20 (that defines an internal intestinal space 22). Hence, the anastomosis device 40 is acting as a fluidic shunt device between the internal gall bladder space 12 and the internal intestinal space 22. Such an implementation may provide a beneficial treatment to the patient when, for example, a flow blockage exists in the native anatomical conduits connecting the internal gall bladder space 12 and the internal intestinal space 22. For example, in some instances the patient may have one or more gallstones that cause a blockage of the patient's cystic duct 14 and/or common bile duct 16. In such a case, the anastomosis device 40 can provide a fluidic passageway such that bile from the gall bladder 10 can flow into the intestine 20. If not for the anastomosis device 40, when bile is blocked from flowing out of the gall bladder 10 cholecystitis (inflammation of the gall bladder 10) may result.

While the anastomosis devices provided herein can be used in some implementations to relieve or prevent cholecystitis as described above, it should be understood that the anastomosis devices provided herein can also be used in many other types of implementations within a patient. For example, the anastomosis devices provided herein can be used in conjunction with various body tissue structures and organs such as, but not limited to, stomachs, colons, small intestines, pancreases, blood vessels, bladders, kidneys, conduits, and the like.

In general, some embodiments of the anastomosis devices provided herein (of which anastomosis device 40 is one example), include a first tissue flange portion 42a, a second tissue flange portion 42b, and a barrel portion 44 therebetween. The barrel portion 44 defines a lumen 46 that extends longitudinally from a first end of the anastomosis device 40 to a second end of the device 40. The lumen 46 acts as a connection (e.g., a shunt passageway) between the internal gall bladder space 12 and the internal intestinal space 22, such that the internal gall bladder space 12 is in fluid communication with the internal intestinal space 22 via the anastomosis device 40.

Figure 2:
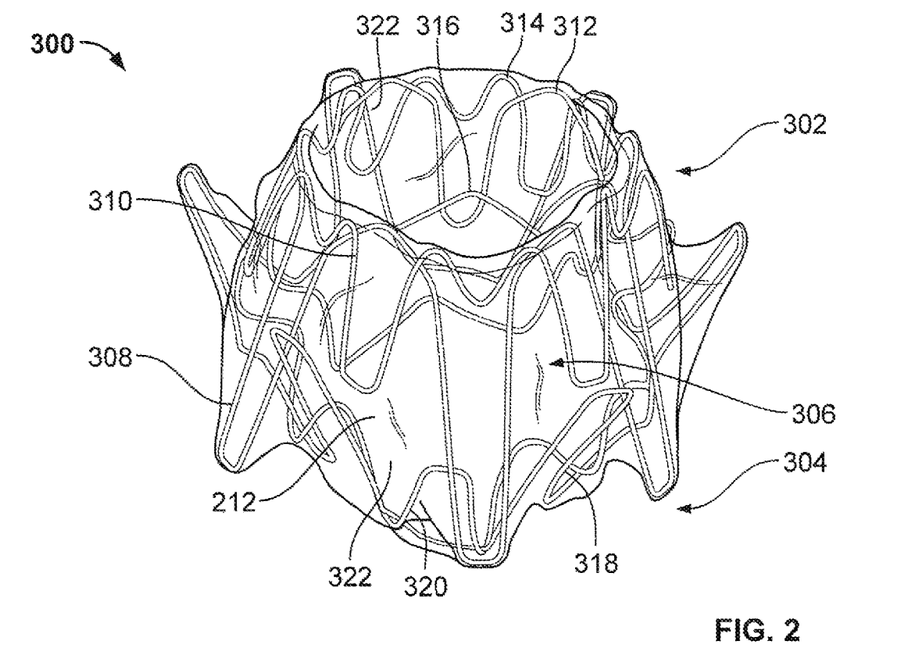
FIG. 2 is a perspective view of another exemplary anastomosis device in accordance with some embodiments.

Referring to FIG. 2, an anastomosis device 300 is shown having a barrel portion 306 or central portion that can be interchangeable with any barrel portion described here, a first flange portion 302, and a second flange portion 304. In some embodiments, the framework of device 300 or any portion thereof can comprise elongate elements such as a spring wire (e.g., L605 steel or stainless steels), shape memory alloy wire (e.g., nitinol or nitinol alloys), superelastic alloy wire (e.g., nitinol or nitinol alloys), other suitable types of wire, or combinations thereof. In the depicted embodiment of device 300, the framework is comprised of an elongate element that is formed by winding, for example. In some embodiments, different types of wires are used at different locations of the device 300. Alternatively, device 300 or portions thereof can be formed from the same piece of precursor material that is cut to create the elongate element framework structure as desired. In some embodiments, device 300 can be formed from a combination of one or more wound wires and one or more cut material portions. In some embodiments, the device 300 or portions thereof may be constructed of polymeric materials. The device 300 is shown with the covering material 212, as described herein.

The first flange portion 302 and the second flange portion 304 are configured to engage one or more layers of tissue therebetween, and to provide apposition forces against the tissue surfaces. The apposition forces provided by the first and second flange portions 302 and 304 can facilitate attachment of the device 300 to the tissue and provide displacement resistance such that the device 300 can reliably remain positioned at a target site in a patient as desired.

The first flange portion 302 and the second flange portion 304 (also referred to herein as apposition portions, flanges, etc.) can each include one or more flange members 308 and 310 (also referred to herein as anchor members, apposition members, fins, etc.). The flange members 308 and 310 can have a variety of different configurations (e.g., lengths, widths, shapes, angles, etc.). In some embodiments two or more flange members have the same configurations. In some embodiments, each of the flange members has the same configuration.

The anastomosis device 300 can be configured in a collapsed low-profile delivery configuration in which the framework is diametrically compressed and longitudinally extended such that the flange members 308 and 310 extend substantially parallel to the longitudinal axis of the device 300. In the deployed or expanded configuration, the flange members 308 and 310 extend from the barrel portion 306. The device 300 may exhibit, for example, beneficial fatigue resistance and elastic properties. In some embodiments, the materials of the device 300 allow the anastomosis devices to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen.

In some embodiments, the length of the flange members 308 and 310 are different in relation to each other to provide both sufficient apposition forces at the base or hole where access is created and migration resistance forces. For example, flange member 308 shown is generally longer than flange member 310. This configuration facilitates a fast and sustainable apposition of tissue to form an anastomosis. In some embodiments, the flange members 308 and 310 of varying lengths are alternated, are staggered, or are nested along the circumferential axis. In some embodiments, the flange members 308 and 310 within each flange portion 302 and/or 304 are uniform in length.

In some embodiments, the lengths of the flange members 308 and 310 are selected based on the size of tissue structures into which the device 300 is to be implanted. For example, if a first body conduit generally includes a smaller geometry than the second body conduit, differing flange lengths can be advantageous. In this example, the flange portion entering the smaller body conduit includes the flanges having a shorter length, while the longer flanges remain in the larger body conduit. The shorter flange length provides an appropriate fit for the smaller body conduit thus ensuring sufficient contact necessary for an anastomosis device, while the longer flanges provide anti-migratory forces that help to retain the device in place. In some embodiments, the short and long flanges are staggered, nested, or separated based on the flange portion.

The anastomosis device 300 (and other embodiments that share design features of the anastomosis device 300) can exhibit the following advantages. Having dissimilar lengths of flange members 308 and 310 can provide apposition at various target locations or zones. Having one or more such specific apposition zones may minimize or eliminate leakage of fluid or other contents that pass through the device lumen. Discrete flange members 308 and 310 designs that move independently of each other leads to better tissue/fin conformability with tissue topography. Better conformability can minimize tissue injury especially when used in a diseased tissue bed. The flexible discrete design of the flange members 308 and 310 can facilitate device 300 removal by folding the flange members 308 and 310 parallel to the lumen of the device 300. This flexibility of the flange members 308 and 310 design can reduce or minimize tissue injury during device removal. Multiple flange members 308 and 310 and short non-overlapping sinusoidal struts on the barrel portion 306 make the device 300 conformable. This conformability helps in easy tracking of the catheter through an endoscope working channel. While providing longitudinal conformability, the short sinusoidal pattern provides adequate radial strength to prevent radial compression of the device 300 by external tissue forces.

The anastomosis device 300 can be formed of one or more elongate members, such as wires in some embodiments. In some embodiments, the anastomosis device 300 can include multiple separate elongate members. For example, the anastomosis device 300 is illustrated in FIG. 2 as including elongate members 312, 314, 316, 318, and 320. The elongate members 312 and 314 can form part of the first flange portion 302, with the elongate member 312 forming the flange members 308 of the first flange portion 302 and the elongate member 314 forming the flange member 310 of the first flange portion 302. The elongate member 316 can form part of a rigid frame of the barrel portion 306 or central portion. The elongate members 318 and 320 can form part of the second flange portion 304, with the elongate member 318 forming the flange members 308 of the second flange portion 304 and the elongate member 320 forming the flange member 310 of the second flange portion 304. Each of the elongate members 312, 314, 316, 318, and 320 can be separate elongate members, connected by the covering material 212. The flange members 308 and 310 can be attached to the covering material 212 to form hinge members 322, allowing the flange members 308 and 310 to pivot with respect to the barrel portion 306 and pivot with respect to the elongate member 316. As the flange members 308 and 310 bend, the hinge members 322 also bend, rotating the hinge members 322 to create a pivoting action of the flange members 308 and 310. Proximal ends of the elongate members 312, 314, 318, and 320 mount in the covering material 212 to form the hinge members 322 pivotably mounted in or on the covering material 212. In some embodiments, the anastomosis device 300 can be formed with no rigid wire extending from the barrel portion 306 through the hinge members 322 to the flange portions 302 and 304. In some embodiments, the hinge members 322 can be more flexible and less rigid than portions of the barrel portion 306 having one or more elongate members 316. In some embodiments, the hinge members 322 can be formed of the covering material 212 without wire material at all as part of the hinge members 322.

In some embodiments, the anastomosis device 300 can include five separate elongate members. For example, two elongate members can comprise the first flange portion 302, such as elongate members 312 and 314, two elongate members can comprise the second flange portion 304, such as elongate members 318 and 320, and one elongate member can comprise the barrel portion 306, such as elongate member 316. Using five separate elongate elements can allow for a relatively strong framework structure while also allowing for relative motion of the first and second flange portions 302 and 304 about the hinge members 322 as described herein.

In some embodiments, the anastomosis device 300 can include three separate elongate members. For example, one elongate member can comprise the first flange portion 302, such as elongate member 312, one elongate member can comprise the second flange portion 304, such as elongate member 318, and one elongate member can comprise the barrel portion 306. In some embodiments, the number of elongate members can be varied as suitable for the application.

In some embodiments, the anastomosis device 300 can include the elongate member 316 forming a rigid frame for the barrel portion 306. The first flange portion 302 can include a plurality of the flange members 310 having a first length and a plurality of the flange members 308 having a second length, the first length being less than the second length. A first hinge member 322 includes the covering material 212 and flexibly couples a first end of the barrel portion 306 and the first flange portion 302. The second flange portion 302 can include a plurality of the flange members 310 and a plurality of the flange members 308. A second hinge member 322 includes the covering material 212 and flexibly couples a second end of the barrel portion 306 and the second flange portion 304.

In some embodiments, forming the flange members 308 and 310 to have different lengths relative to each other can allow for the anastomosis device 300 to have its strength tailored for a particular application. In some embodiments, length of the flange members 308 and/or 310 can be increased to distribute force over a greater area and apply less localized force. In some embodiments, length of the flange members 308 and/or 310 can be shortened to distribute force over a smaller area and apply greater localized force. In some embodiments, length of the flange members 308 can be increased to distribute force over a greater area and apply less localized force while length of the flange members 310 can be shortened to distribute force over a smaller area and apply greater localized force.

In some embodiments, the anastomosis device 300 can be substantially symmetric about a centerline axis. In some embodiments, the anastomosis device 300 need not be symmetric, but rather, length of specific flange members 308 and/or 310 can be shortened and/or lengthened as appropriate for a given application to increase localized force at one location and decrease localized force at another location. This can be allow for anastomosis device 300 to be tailored for particular applications, such as an application with diseased tissue benefiting from a particular force distribution. In applications with diseased tissue, the anastomosis device 300 can be designed to apply reduced force in an area of that diseased tissue, such as by using elongated flange members 308. In some embodiments, the flange members 308 and 310 of the first flange portion 302 can provide force at a different location on a layer of tissue than a location of an apposed force applied by the flange members 308 and 310 of the second flange portion 304.

In some embodiments, other variables relating to the flange members 308 and 310 can be varied in addition to length in order to vary force distribution. For example, the wire diameter of one, some, or all of the flange members 308 and 310 can be increased or decreased. As an additional example, the projection angle of one, some, or all of the flange members 308 and 310 can be increased or decreased. As an additional example, the number of one, some, or all of the flange members 308 and 310 can be increased or decreased. As an additional example, the material stiffness of one, some, or all of the flange members 308 and 310 can be increased or decreased. One or more of these variables can be varied in one or more flange members 308 and 310 in addition to or instead of varying length so as to vary force distribution of the flange portions 302 and 304.

In some embodiments, the flange members 308 have a length of about 10 to 15 millimeters. In some embodiments, the flange members 310 have a length of about 5 to 10 millimeters. In some embodiments, the barrel portion 306 has a barrel length of about 5 to 15 millimeters from its first end to its second end, and a barrel diameter of about 10 to 25 millimeters. In some embodiments, the elongate members 312, 314, 316, 318, and 320 can have diameters of between about 0.008 inches (0.02032 centimeters) to 0.012 inches (0.03048 centimeters). In some embodiments, dimensions can be varied as suitable for the application.

In some embodiments, the anastomosis device 300 can include the barrel portion 306 including a rigid frame having a first end and a second end. The first flange portion 302 can include a plurality of the flange members 308 having a first length and a plurality the flange members 310 having a second length. One of the hinge members 322 can include the cover material 212 and can flexibly couple the first end of the barrel portion 306 and the first flange portion 302. The second flange portion 304 can include a plurality of the flange members 308 having a third length and a plurality of the flange members 310 having a fourth length. Another hinge member 322 can flexibly couple the second end of the barrel portion 306 and the second flange portion 304. The first length can be less than the second length. At least one of the first length and the second length can be different from at least one of the third length and the fourth length. In some embodiments, both of the first length and the second length can be different from at least one of the third length and the fourth length. In some embodiments, both of the first length and the second length can be different from both of the third length and the fourth length.

In some embodiments, the anastomosis device 300 includes the barrel portion 306 having a rigid framework and having a first end and a second end. The first flange portion 302 can include a plurality of the flange members 308 having a first projecting angle and a plurality the flange members 310 having a second projecting angle. One of the hinge members 322 can include the cover material 212 and can flexibly couple the first end of the barrel portion 306 and the first flange portion 302. The second flange portion 304 can include a plurality of the flange members 308 having the first projecting angle and a plurality the flange members 310 having the second projecting angle. Another hinge member 322 can flexibly couple the second end of the barrel portion 306 and the second flange portion 304. In some embodiments, the first projecting angle is different than the second projecting angle. In some embodiments, the first projecting angle is equal to the second projecting angle.

In some embodiments, the flange members 308 and 310 can extend from the barrel portion 306 by an angle that is less than 90 degrees in a relaxed state. In some embodiments, the flange members 308 can extend from the barrel portion 306 by an angle of between about 10 degrees and about 90 degrees in a relaxed state. In some embodiments, the flange members 310 can extend from the barrel portion 306 by an angle of between about 5 degrees and about 80 degrees in a relaxed state. In some embodiments, the flange members 308 can extend from the barrel portion 306 by an angle of about 30 degrees in a relaxed state. In some embodiments, the flange members 310 can extend from the barrel portion 306 by an angle of about 10 degrees in a relaxed state. In some embodiments, dimensions and geometries can be varied as suitable for the particular application.

In some embodiments, the covering material 212 can cover substantially all of the device 300, including all of the flange portions 302 and 304 as well as the barrel portion 306. In some embodiments, the covering material 212 can cover less than all of the device 300. In some embodiments, the covering material 212 can be formed by a single sheet of material covering the device 300. In other embodiments, the covering material 212 can be formed by multiple separate sheets of material. For example, in some embodiments the covering material 212 can include a first sheet of material covering the flange members 308 of the flange portion 302 and a second sheet of material covering the flange members 310 of the flange portion 302. In some embodiments, the second sheet of material does not cover the first flange members 308. In some embodiments, the covering material 212 can also have a third sheet of material covering the barrel portion 306, a fourth sheet of material covering the flange members 308 of the flange portion 304, and a fifth sheet of material covering the flange members 310 of the flange portion 304. This can enable a design with different covering materials 212 for each length of the flange members 308 and 310 in a given one of the flange portions 302 or 304.

Suitable materials for the elongate elements of the devices provided herein include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return to the frame's original form without deformation. In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as drawn filled tube where the outer layer is constructed of nitinol and the inner core is a radiopaque material such as platinum or tantalum. In this construct, the outer layer provides the super-elastic properties and the inner core remains elastic due to lower bending stresses.

In some embodiments, the elongate elements used to construct the devices provided herein can be treated in various ways to increase the radiopacity of the devices for enhanced radiographic visualization. In some embodiments, the devices are at least partially a drawn-filled type of NiTi containing a different material at the core, such as a material with enhanced radiopacity. In some embodiments, the devices include a radiopaque cladding or plating on at least portions of the first flange portion, the second flange portion, and the barrel portion. In some embodiments, one or more radiopaque markers are attached to the devices. In some embodiments, the elongate elements and/or other portions of the devices provided herein are also visible via ultrasound.

In some embodiments, the first flange portion 302, the second flange portion 304, and the barrel portion 306, can comprise a framework of interconnected elongate elements that is constructed by cutting a tube. In one such embodiment, a tube of metallic material (e.g., nitinol, stainless steel, cobalt, etc.) can be laser cut, and then the tube is expanded and shaped into the desired configuration. In some such embodiments, the metallic material is heat-set in the desired configuration so that the material receives a shape-memory whereby the material will naturally strive to attain the desired configuration. In some embodiments, shape memory materials such as nitinol may strive to attain the desired configuration when exposed to body temperature.

As described further below, a covering material 212 can be disposed on some portions or on all of the first flange portion 302, the second flange portion 304, and/or the barrel portion 306. In some embodiments, portions of the first flange portion 302, the second flange portion 304, and/or the barrel portion 306 can remain free of the covering material 212.

In some embodiments, the materials and configuration of the anastomosis device 300 (and the other anastomosis device embodiments provided herein) allow the devices to be elastically crushed, folded, and/or collapsed into a low-profile delivery configuration for containment within a lumen for transcatheter or endoscopic/thorascopic delivery, and to self-expand to an operative size and configuration once positioned at a desired target site within a body and deployed from the lumen. For example, the anastomosis device 300 can be configured in a collapsed delivery configuration in which the plurality of struts 308 are radially compressed such that they are forced to extend substantially parallel to the axis of the barrel portion 306, and in which the diameter of the barrel portion 306 is also crushed to become smaller. Due to the use of such materials and structure, the device 300 may also exhibit, for example, beneficial fatigue resistance and elastic properties.

After deployment, the plurality of struts 308 extend from the barrel portion 306 at a radial orientation and geometry to exert a desired level of apposition pressure on the tissue. In some embodiments, the plurality of struts 308 extend from the barrel portion 306 such that the nominal measure of the angle between the struts 308 and the longitudinal axis of the device 300 is about 100°, or about 90°, or about 80°, or about 70°, or about 60°, or about 50°, or about 40°, or about 30°, or about 20°, or about 10°, and the like. In some embodiments, the plurality of struts 308 extend from the barrel portion 306 such that the nominal measure of the angle between the struts 308 and the longitudinal axis of the device 300 is in a range from about 80 ° to about 100°, or about 70° to about 90°, or about 60° to about 80°, or about 50° to about 70°, or about 40° to about 60°, or about 30° to about 50°, or about 20° to about 40°, or about 10° to about 30°.

The flange member 308 and 310 can comprise a variety of materials including, but not limited to, metallic shape memory materials and super-elastic alloys. Thus, the flange member 308 and 310 can be configured to self-expand to an expanded deployed configuration, e.g., including to a predetermined angle.

The barrel portion 306 is shown in a deployed or expanded configuration. In some embodiments, the barrel portion 306, as described above, can comprise a variety of metallic shape memory materials and super-elastic alloys. Thus, the barrel portion 306 can be configured to self-expand to the deployed configuration. In some embodiments, the barrel portion 306 is balloon expandable to the deployed configuration, or supplemental expansion forces can be applied to a self-expandable device by balloon dilation. The diameter of the barrel portion 306 can be made in any size as desired in order to suit the intended use and/or delivery system of the anastomosis device 300. For example, in the low-profile delivery configuration the anastomosis device 300 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. When the anastomosis device 300 is configured in its expanded deployed configuration as shown, the diameter of the barrel portion 306 increases to a deployed diameter, in some implementations, the deployed outer diameter of the barrel portion 306 is configured to at least partially anchor the device 300 via an interference fit with the tissue aperture in which the barrel portion 306 resides. However, in some implementations the deployed outer diameter of the barrel portion 306 is slightly less than the diameter of the tissue aperture in which the barrel portion 306 resides, and the flange portions 302 and 304 compress the tissue to provide the migration resistance. In some embodiments, the fully expanded diameter of the barrel portion 306 is about 30 mm, or about 25 mm, or about 20 mm, or about 15 mm, or about 12 mm, or about 10 mm, or about 8 mm, or about 6 mm, or about 4 mm, and the like. In some embodiments, the fully expanded diameter of the barrel portion 306 is in a range between about 20 mm to about 30 mm, or about 15 mm to about 25 mm, or about 10 mm to about 20 mm, or about 5 mm to about 15 mm, or about 4 mm to about 8 mm, and the like.

The anastomosis device 300 also includes the covering material 212. In some embodiments, the covering material 212 is disposed on at least some portions (or on all) of the first flange portion 302, the second flange portion 304, and the barrel portion 306. In some embodiments, some portions of the first flange portion 302, the second flange portion 304, and/or the barrel portion 306 are not covered by the covering material 212.

In some embodiments, the covering material 212 is generally fluid impermeable. That is, in some embodiments the covering material 212 may be made of a material that inhibits or reduces passage of blood, bile and/or other bodily fluids and materials through the covering material 212 itself. In some embodiments, the covering material 212 has a material composition and configuration that inhibits or prevents tissue ingrowth and/or endothelialization or epithelialization into the covering material 212. Some such embodiments that are configured to inhibit or prevent tissue ingrowth and/or endothelialization can be more readily removed from the patient at a future date if so desired. In some embodiments, the covering material 212, or portions thereof, has a microporous structure that provides a tissue ingrowth scaffold for durable sealing and/or supplemental anchoring strength of the anastomosis device 300.

In some embodiments, the covering material 212 comprises a fluoropolymer, such as an expanded polytetrafluoroethylene (ePTFE) polymer or polyvinylidene difluoride (PVDF) polymer. In some embodiments, the covering material 212 comprises a polyester, a silicone, a urethane, another biocompatible polymer, polyethylene terephthalate (e.g., Dacron®), bioabsorbable materials, copolymers, or combinations and subcombinations thereof. In some embodiments, the covering material 212 comprises a bioabsorbable web. In some embodiments, the bioabsorbable material can also provide an anti-migration feature by promoting attachment between the device 300 and tissue until the bioabsorbable material is absorbed.

In some embodiments, the covering material 212 (or portions thereof) is modified by one or more chemical or physical processes that enhance one or more properties of the material 212. For example, in some embodiments, a hydrophilic coating may be applied to the covering material 212 to improve the wettability and echo translucency of the material 212. In some embodiments, the covering material 212, or portions thereof, may be modified with chemical moieties that facilitate one or more of endothelial cell attachment, endothelial cell migration, endothelial cell proliferation, and resistance to or promotion of thrombosis. In some embodiments, the covering material 212, or portions thereof, may be modified to resist biofouling. In some embodiments, the covering material 212, or portions thereof, may be modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance is a corticosteroid, a human growth factor, an anti-mitotic agent, an antithrombotic agent, a stem cell material, or dexamethasone sodium phosphate, to name some embodiments. In some embodiments, a pharmacological agent may be delivered separately from the covering material 212 to the target site to promote tissue healing or tissue growth.

Coatings and treatments may be applied to the covering material 212 before or after the covering material 212 is joined or disposed on the framework of the anastomosis device 300. Additionally, one or both sides of the covering material 212, or portions thereof, may be coated. In some embodiments, certain coatings and/or treatments are applied to the covering material(s) 212 located on some portions of the anastomosis device 300, and other coatings and/or treatments are applied to the material(s) 212 located on other portions of the anastomosis device 300. In some embodiments, a combination of multiple coatings and/or treatments are applied to the covering material 212, or portions thereof. In some embodiments, certain portions of the covering material 212 are left uncoated and/or untreated. In some embodiments, the device 300 is fully or partially coated to facilitate or frustrate a biological reaction, such as, but not limited to, endothelial cell attachment, endothelial cell migration, endothelial cell proliferation and resistance to or promotion of thrombosis.

In some embodiments, a first portion of the covering material 212 is formed of a first material and a second portion of the covering material 212 is formed of a second material that is different than the first material. In some embodiments, the covering material 212 is comprised of multiple layers of materials, which may be the same or different materials. In some embodiments, portions of the covering material 212 have one or more radiopaque markers attached thereto to enhance in vivo radiographic visualization of the anastomosis device 300, or one or more echogenic areas to enhance ultrasonic visibility.

In some embodiments, one or more portions of the covering material 212 are attached to the framework of the device 300, such as the barrel portion 306 and/or the flange portions 302 and 304. The attachment can be accomplished by a variety of techniques such as, but not limited to, stitching the covering material 212 to the framework of the device 300, adhering the covering material 212 to the framework of the device 300, laminating multiple layers of the covering material 212 to encompass portions of the elongate members of the device 300, using clips or barbs, laminating multiple layers of the covering material together through openings in the framework of the device 300. In some embodiments, the covering material 212 is attached to the framework of the device 300 at a series of discrete locations thereby facilitating the flexibility of the framework. In, some embodiments, the covering material 212 is attached to the framework of the device 300 loosely. In some embodiments, the covering material 212 is attached to the framework using other such techniques or combinations of such techniques.

In some embodiments, the framework of the device 300 (or portions thereof) is coated with a bonding agent (e.g., fluorinated ethylene propylene (FEP) or other suitable adhesive) to facilitate attachment of the covering material 212 to the framework. Such adhesives may be applied to the framework using contact coating, powder coating, dip coating, spray coating, or any other appropriate means.

Figure 3:
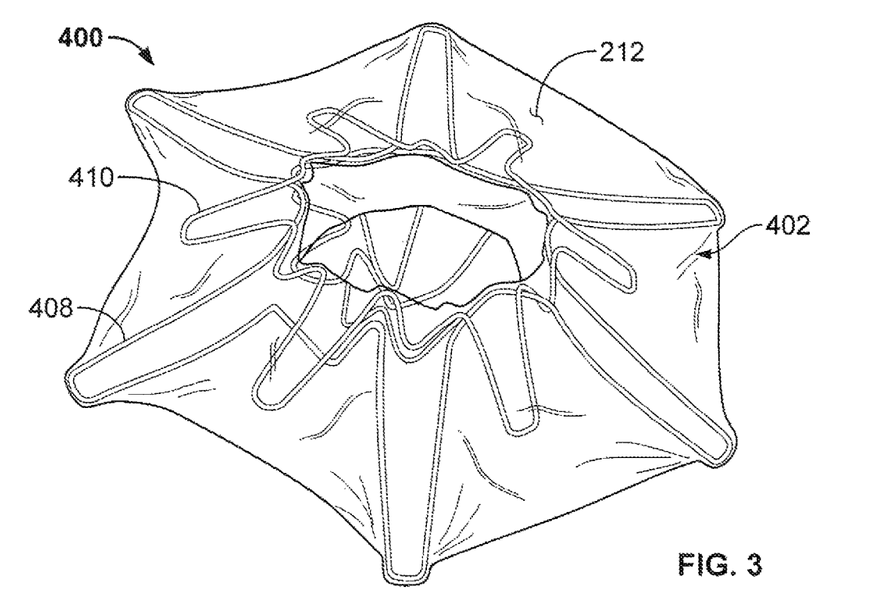
FIG. 3 is a perspective view of another exemplary anastomosis device in accordance with some embodiments.
Figure 4A:
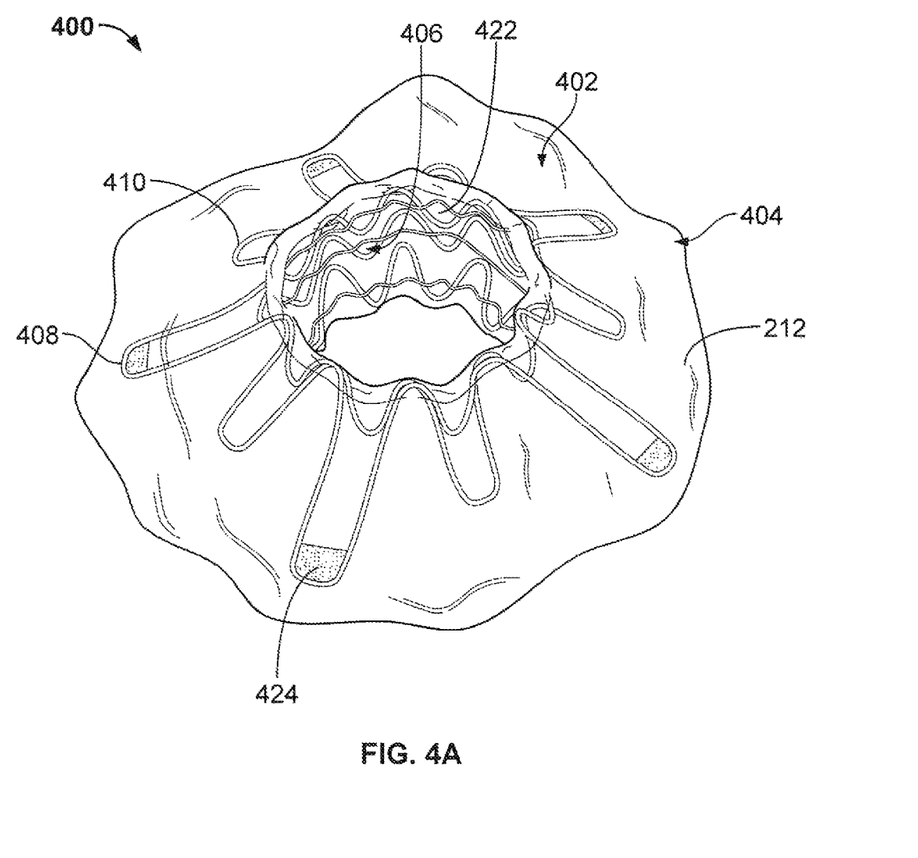
FIG. 4A is a perspective view of another exemplary anastomosis device in accordance with some embodiments.

FIGS. 3 and 4A are perspective views of another exemplary anastomosis device 400 in accordance with some embodiments. The anastomosis device 400 is shown having a first flange portion 402, a second flange portion 404, a barrel portion 406, and covering material 212. The first flange portion 402 and the second flange portion 404 (also referred to herein as flange portions, flanges, etc.) can each include one or more flange members 408 and 410 (also referred to herein as anchor members, apposition members, fins, etc.). The flange members 408 and 410 can have different configurations (e.g., lengths, widths, shapes, angles, etc.). The covering material 212 can form hinge members 422, allowing the flange members 408 and 410 to pivot with respect to the barrel portion 406. In some embodiments, the anastomosis device 400 can have features and functionality similar to that described with respect to anastomosis device 300 and other anastomosis devices described herein.

In some embodiments, such as shown in FIG. 4A, one or more of the flange members 408 can include radiopaque markers 424 at distal regions thereof. In some embodiments, the anastomosis device 400 can include radiopaque markers 424 on some but not all flange members of the anastomosis device. For example, in the illustrated embodiment, the anastomosis device 400 includes radiopaque markers 424 at distal regions of the flange members 408 but not at the distal ends of any of the flange members 406. In some embodiments, the position of the radiopaque markers 424 can be varied as suitable for the application.

Figure 4B:
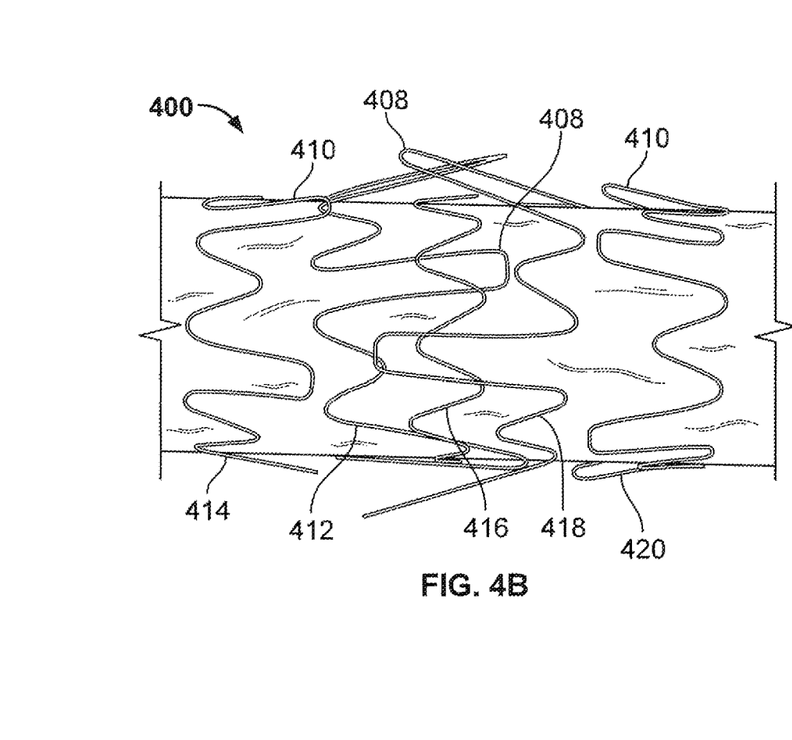
FIG. 4B is an exploded view of the anastomosis device of FIG. 4A.

FIG. 4B is an exploded view of the anastomosis device 400 with the covering material 212 removed. The anastomosis device can include elongate members 412, 414, 416, 418, and 420. In the illustrated embodiment, the anastomosis device 400 includes five separate elongate members. The elongate member 412 defines the flange members 408 of the first flange portion 402. The elongate member 414 defines the flange members 410 of the first flange portion 402. The elongate member 416 defines a rigid frame of the barrel portion 406. The elongate member 418 defines the flange members 408 of the second flange portion 404. The elongate member 420 defines the flange members 410 of the second flange portion 404. Two elongate members 412 and 414 support the first flange portion 402, two elongate members 418 and 420 support the second flange portion 404, and one elongate member 416 supports the barrel portion 406. Thus, the separate elongate members 412, 414, 416, 418, and 420 can combine with the covering material 212 to form the anastomosis device 400. The elongate members 412, 414, 416, 418, and 420 can combine such that the flange members 408 alternate with the flange members 410. Hinges for the flange members 408 can align with the flange members 410 and hinges for the flange members 410 can align with the flange members 408. Accordingly, each of the flange members 408 and 410 can hinge separately.

Figure 5:
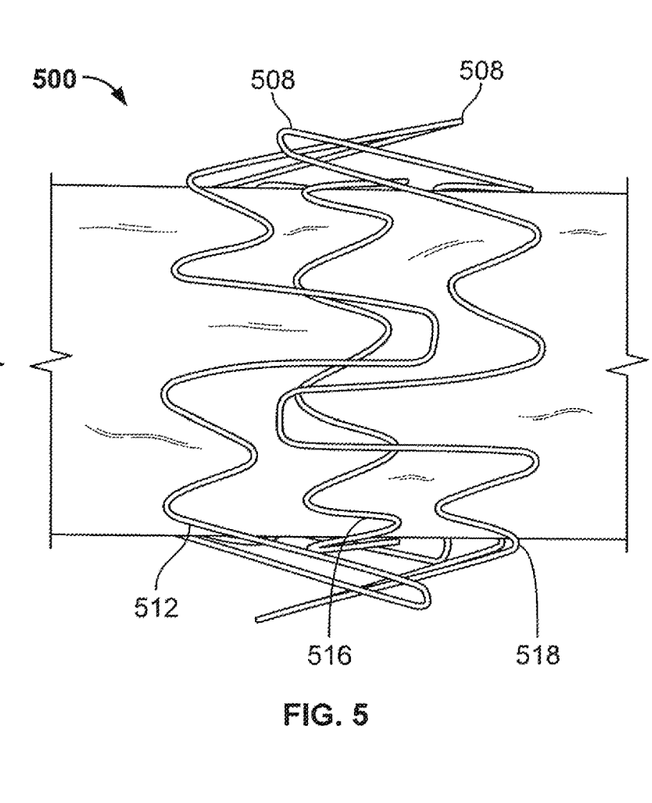
FIG. 5 is an exploded view of another exemplary anastomosis device in accordance with some embodiments.

FIG. 5 is an exploded view of another exemplary anastomosis device 500 in accordance with some embodiments. The anastomosis device 500 can include flange members 508 and elongate members 512, 516, and 518. In the illustrated embodiment, the anastomosis device 500 includes three separate elongate members. The elongate member 512 defines the flange members 508 of a first flange portion. The elongate member 516 defines a rigid frame of a barrel portion. The elongate member 518 defines the flange members 508 of a second flange portion. In the anastomosis device 500, one elongate member 512 supports the first flange portion, one elongate member 518 supports the second flange portion, and one elongate member 516 support the barrel portion. Thus, the separate elongate members 512, 516, and 518 can combine with the covering material 212 (not shown in FIG. 5) to form the anastomosis device 500. The anastomosis device 500 has features and functionality similar or identical to that described with respect to anastomosis device 300.

Figure 6:
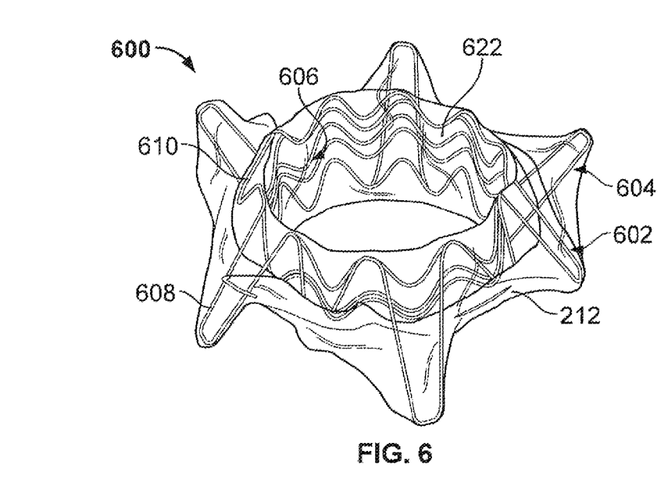
FIG. 6 is a perspective view of another exemplary anastomosis device in accordance with some embodiments.

FIG. 6 is a perspective view of another exemplary anastomosis device 600 in accordance with some embodiments. The anastomosis device 600 is shown having a first flange portion 602, a second flange portion 604, a barrel portion 606, and covering material 212. The first flange portion 602 and the second flange portion can each include one or more flange members 608 and 610. The flange members 608 and 610 can have different configurations (e.g., lengths, widths, shapes, angles, etc.). The covering material 212 can form the hinge members 622, allowing the flange members 608 and 610 to pivot with respect to the barrel portion 606. In some embodiments, the covering 212 need not cover all of the flange members 708. The anastomosis device 600 has features and functionality similar or identical to that described with respect to anastomosis device 300.

Figure 7:
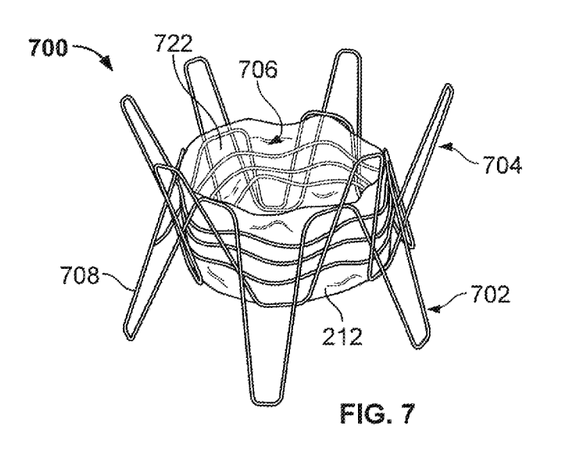
FIG. 7 is a perspective view of another exemplary anastomosis device in accordance with some embodiments.

FIG. 7 is a perspective view of another exemplary anastomosis device in accordance with some embodiments. The anastomosis device 700 is shown having a first flange portion 702, a second flange portion 704, a barrel portion 706, and covering material 212. The first flange portion 702 and the second flange portion can each include one or more flange members 708. The flange members 708 can have different configurations (e.g., lengths, widths, shapes, angles, etc.). The covering material 212 can form the hinge members 722, allowing the flange members 708 to pivot with respect to the barrel portion 706. In some embodiments, the covering 212 need not cover all of the flange members 708. In some embodiments, the anastomosis device 700 can include flange members 708 having a substantially common length around each respective flange portion 702 and 704, as opposed to alternating long and short flange members 708. In some of such embodiments, angle of the flange members 708 can be varied. In some embodiments, length of the flange members 708 can be varied. For example, length of the flange members 708 can be varied symmetric or asymmetrically. The anastomosis device 700 has features and functionality similar or identical to that described with respect to anastomosis device 300.

Figure 8:
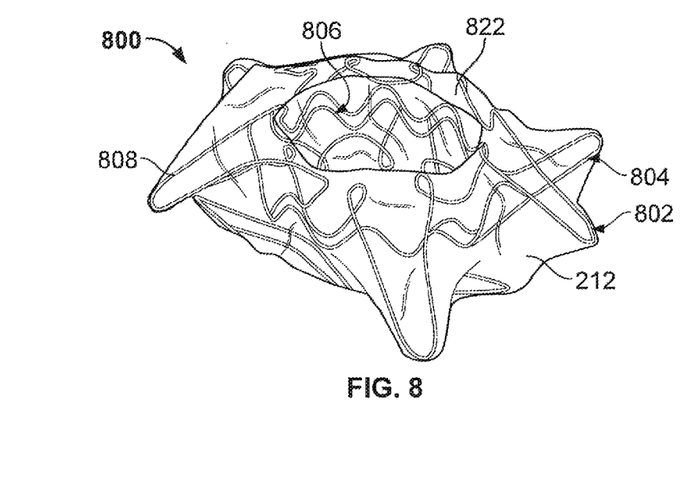
FIG. 8 is a perspective view of another exemplary anastomosis device in accordance with some embodiments.

FIG. 8 is a perspective view of another exemplary anastomosis device in accordance with some embodiments. The anastomosis device 800 is shown having a first flange portion 802, a second flange portion 804, a barrel portion 806, and covering material 212. The first flange portion 802 and the second flange portion can each include one or more flange members 808. The flange members 808 can have different configurations (e.g., lengths, widths, shapes, angles, etc.). The covering material 212 can form the hinge members 822, allowing the flange members 808 to pivot with respect to the barrel portion 806. In some embodiments, the anastomosis device 800 can include flange members 808 having a substantially common length around each respective flange portion 802 and 804, as opposed to alternating long and short flange members 808. In some of such embodiments, angle of the flange members 808 can be varied. In some embodiments, length of the flange members 808 can be varied in a manner similar to embodiments discussed above. For example, length of the flange members 808 can be varied symmetric or asymmetrically. The anastomosis device 800 has features and functionality similar or identical to that described with respect to anastomosis device 300.

Figure 9:
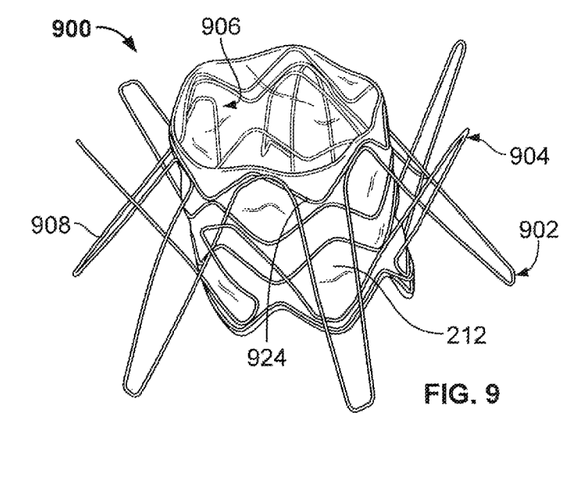
FIG. 9 is a perspective view of another exemplary anastomosis device in accordance with some embodiments.

FIG. 9 is a perspective view of another exemplary anastomosis device in accordance with some embodiments. The anastomosis device 900 is shown having a first flange portion 902, a second flange portion 904, a barrel portion 906, and covering material 212. The first flange portion 902 and the second flange portion can each include one or more flange members 908. The flange members 908 can have different configurations (e.g., lengths, widths, shapes, angles, etc.). In some embodiments, the covering 212 need not cover all of the flange members 908. In some embodiments, the anastomosis device 900 can include one or more additional reinforcement elongate members 924 to reduce or prevent buckling at a connection point between the flange members 908 and the barrel portion 906. The reinforcement elongate members 924 can reduce or prevent pivoting action by the flange members 908 and reinforce the barrel portion 906 as well as the flange portions 902 and 904. The reinforcement elongate members 924 can reduce or prevent narrowing of the anastomosis device 900 post implantation. Apposition forces can be higher than in embodiments with hinge portions due to connection of the reinforcement elongate members 924 at proximal ends of the flange members 908. The anastomosis device 900 can have features and functionality similar or identical to that described with respect to anastomosis device 300.

Figures 10, 11, 12:
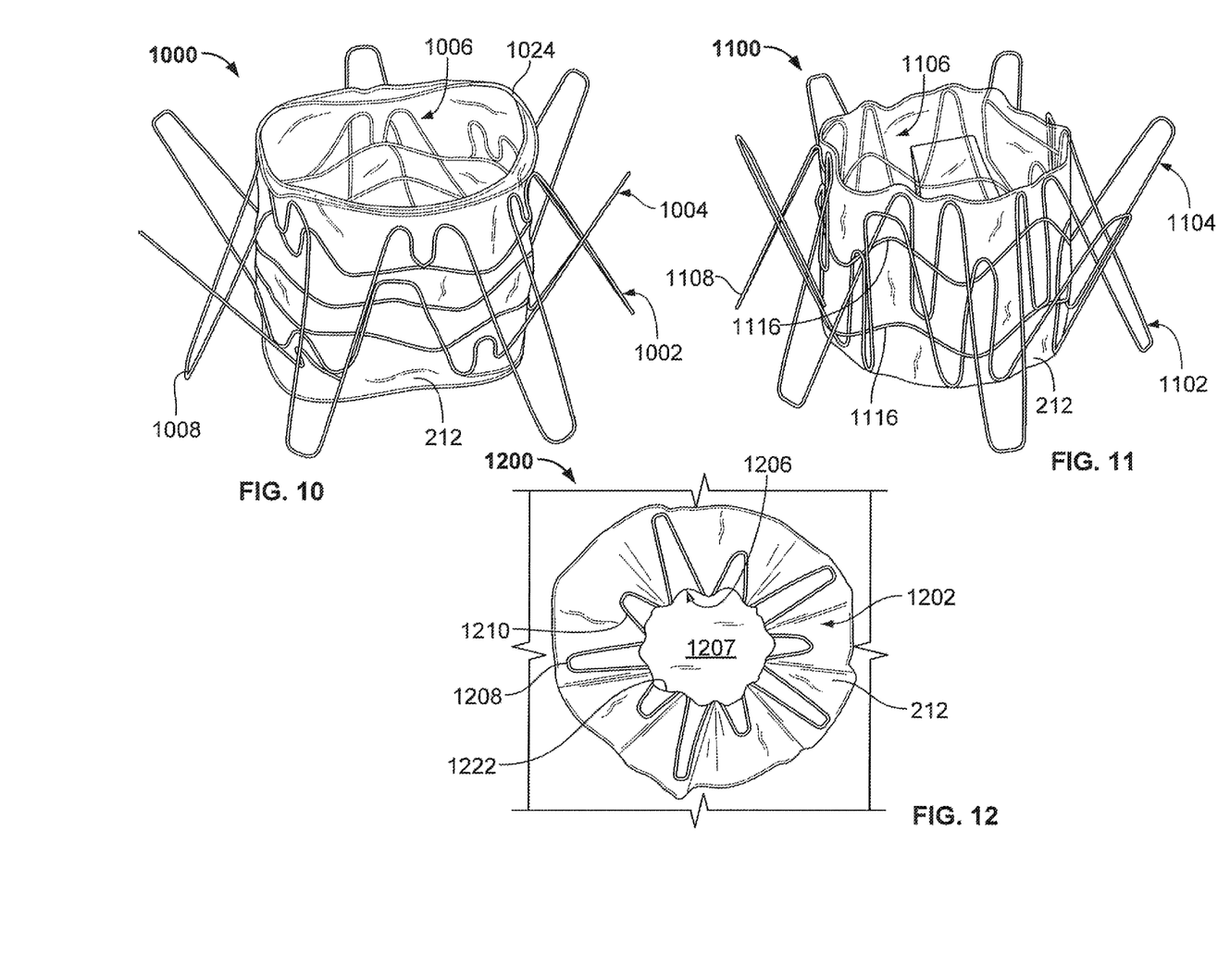
FIG. 10 is a perspective view of another exemplary anastomosis device in accordance with some embodiments.
FIG. 11 is a perspective view of another exemplary anastomosis device in accordance with some embodiments.
FIG. 12 is a side view of another exemplary anastomosis device in accordance with some embodiments.

FIG. 10 is a perspective view of another exemplary anastomosis device in accordance with some embodiments. The anastomosis device 1000 is shown having a first flange portion 1002, a second flange portion 1004, a barrel portion 1006, and covering material 212. The first flange portion 1002 and the second flange portion can each include one or more flange members 1008. The flange members 1008 can have different configurations (e.g., lengths, widths, shapes, angles, etc.). In some embodiments, the anastomosis device 1000 can include one or more additional reinforcement elongate members 1024 positioned at or proximate a rim of the barrel portion 1006. The reinforcement elongate members 1024 can reduce or prevent pivoting action by the flange members 1008 and reinforce the barrel portion 1006 as well as the flange portions 1002 and 1004. The reinforcement elongate members 1024 can provide a straighter edge for the anastomosis device 1000 and can reduce or prevent narrowing of the anastomosis device 1000 post implantation. Apposition forces can be higher than in embodiments with hinge portions. In some embodiments, the covering 212 need not cover all of the flange members 1008. The anastomosis device 1000 has features and functionality similar or identical to that described with respect to anastomosis device 300.

FIG. 11 is a perspective view of another exemplary anastomosis device in accordance with some embodiments. The anastomosis device 1100 is shown having a first flange portion 1102, a second flange portion 1104, a barrel portion 1106, and covering material 212. The first flange portion 1102 and the second flange portion can each include one or more flange members 1108. The flange members 1108 can have different configurations (e.g., lengths, widths, shapes, angles, etc.). In some embodiments, the covering 212 need not cover all of the flange members 1108. The flange members 1108 can connect directly to one or more elongate members 1116 that form a rigid frame for the barrel portion 1106. This connection can reduce or prevent buckling at a connection point between the flange members 1108 and the barrel portion 1106. This connection can reduce or prevent pivoting action by the flange members 1108 and reinforce the barrel portion 1106 as well as the flange portions 1102 and 1104. This connection can reduce or prevent narrowing of the anastomosis device 1100 post implantation. Apposition forces can be higher than in embodiments with hinge portions due to connection of the flange members 1108 to the elongate members 1116 at proximal ends of the flange members 1108. The anastomosis device 1100 has features and functionality similar or identical to that described with respect to anastomosis device 300.

FIG. 12 is a side view of another exemplary anastomosis device 1200 in accordance with some embodiments. The anastomosis device 1200 is shown having a first flange portion 1202, a barrel portion 1206, and covering material 212. The first flange portion 1202 includes flange members 1208 and 1210. The flange members 1208 and 1210 can have different configurations (e.g., lengths, widths, shapes, angles, etc.). In FIG. 12, the anastomosis device is shown deployed and expanded, as if in an operative site of a patient. Consequently, the second flange portion (not shown) is obscured in FIG. 12. The covering material 212 can form the hinge members 1222, which can allow the flange members 1208 and 1210 to pivot with respect to the barrel portion 1206 to the deployed position shown in FIG. 12. The anastomosis device 1200 has features and functionality similar or identical to that described with respect to anastomosis device 300.

In some embodiments, the devices provided herein can be used for sealing or anchoring a heart valve implant. A heart valve implant enables one-way flow of blood from a heart chamber and usually has a first inflow end and a second outflow end. The contractions of the heart cause flow of blood through the valve from the inflow end to the outflow end. Between the inflow and outflow ends, a valve assembly within the heart valve implant provides for one way flow, opening to allow flow from the inflow to the outflow end when the pressure of the blood is higher on the inflow end, and closing to prevent flow when the pressure on the outflow end is higher than the inflow end. In some embodiments, the device includes a tunnel or central aperture through the device with apposition portions to anchor a valve assembly and seal against backward flow. A valve assembly can be attached in the tunnel or central aperture. The apposition portions of the device can be configured to be highly conformable to the topography of the heart chambers or blood vessels, and compliant with the beating movements of the heart. In some embodiments, a covering material is configured to allow flow through a valve assembly in the tunnel or aperture while preventing flow around the apposition portions.

It should be understood that one or more design features of the anastomosis devices provided herein can be combined with other features of other anastomosis devices provided herein. In effect, hybrid designs that combine various features from two or more of the anastomosis device designs provided herein can be created, and are within the scope of this disclosure.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device comprising:
   a barrel portion comprising a rigid frame having a first end and a second end;
   a first flange portion, said first flange portion comprising a plurality of first flange members having a first length and a plurality of second flange members having a second length, said first length being less than said second length, said plurality of first flange members being discrete and separate from said plurality of second flange members;
   a first hinge member formed of a cover material and flexibly coupling said first end of said barrel portion and said first flange portion, said cover material allowing said first flange portion to pivot with respect to said barrel portion;
   a second flange portion, said second flange portion comprising a plurality of said first flange members and a plurality of said second flange members;
   a second hinge member formed of said cover material and flexibly coupling said second end of said barrel portion and said second flange portion, said cover material allowing said second flange portion to pivot with respect to said barrel portion; and
   a plurality of elongate members forming part of the rigid frame of the barrel portion, part of the first flange portion, and part of the second flange portion without the plurality of elongate members extending from the barrel portion through the first hinge member to the first flange portion and from the barrel portion through the second hinge member to the second flange portion.

2. The implantable medical device of claim 1, wherein said first flange members extend radially from said first and second hinge members at an angle less than 80 degrees and said second flange members extend radially from said first and second hinge members at an angle less than 90 degrees.

3. The implantable medical device of claim 1, wherein said plurality of first flange members comprises a first elongate member having a first geometry and said plurality of second flange members comprises a second elongate member having a second geometry different than the first geometry.

4. The implantable medical device of claim 3, wherein said first elongate member has a first stiffness and said second elongate member has a second stiffness different than the first stiffness.

5. The implantable medical device of claim 1, wherein said barrel portion comprises an elongate member having a first stiffness and said first and second flange portions each comprise one or more elongate members having a second stiffness different than the first stiffness.

6. The implantable medical device of claim 5, wherein said elongate member is a wire.

7. The implantable medical device of claim 1, wherein said cover material is selected from the group consisting of a fluoropolymer film, expanded polytetrafluoroethylene, polyester, a silicone, a urethane, another biocompatible polymer, polyethylene terephthalate, bioabsorbable systems, and copolymers.

8. The implantable medical device of claim 1, wherein said first flange portion provides a first apposition force and said second flange portion provides a second apposition force different than said first apposition force.

9. The implantable medical device of claim 1, wherein said plurality of first flange members provides a first apposition force and said plurality of second flange members provides a second apposition force different than said first apposition force.

10. The implantable medical device of claim 1, wherein at least a portion of said first flange portion and at least a portion of said second flange portion are covered with said cover material.

11. The implantable medical device of claim 1, wherein the cover material comprises a first sheet of material covering the plurality of first flange members of the first flange portion and a second sheet of material covering the plurality of second flange members of the first flange portion, wherein the second sheet of material does not cover the first flange members of the first flange portion.

12. The implantable medical device of claim 11, wherein the cover material comprises a third sheet of material covering the plurality of first flange members of the second flange portion and a fourth sheet of material covering the plurality of second flange members of the second flange portion, wherein the third sheet of material does not cover the first flange members of the second flange portion.

13. An implantable medical device comprising:
   a barrel portion comprising a rigid frame having a first end and a second end;
   a first flange portion, said first flange portion comprising a plurality of first flange members having a first length and a plurality of second flange members having a second length, said plurality of first flange members being discrete and separate from said plurality of second flange members;

a first hinge member formed of a cover material and flexibly coupling said first end of said barrel portion and said first flange portion, said cover material allowing said first flange portion to pivot with respect to said barrel portion;

a second flange portion, said second flange portion comprising a plurality of third flange members having a third length and a plurality of fourth flange members having a fourth length;

a second hinge member formed of said cover material and flexibly coupling said second end of said barrel portion and said second flange portion, said cover material allowing said second flange portion to pivot with respect to said barrel portion, and a plurality of elongate members forming part of the rigid frame of the barrel portion, part of the first flange portion, and part of the second flange portion without the plurality of elongate members extending from the barrel portion through the first hinge member to the first flange portion and from the barrel portion through the second hinge member to the second flange portion;

wherein said first length is less than said second length and said third length is less than said fourth length, and wherein at least one of said first length and said second length is different from at least one of said third length and said fourth length.

14. The implantable medical device of claim 13, wherein said first flange members extend radially from said first and second hinge members at an angle less than 80 degrees and said second flange members extend radially from said first and second hinge members at an angle less than 90 degrees.

15. The implantable medical device of claim 13, wherein said plurality of first flange members extends radially from said first hinge member at an angle of between about 5 degrees and about 80 degrees, said plurality of second flange members extends radially from said first hinge member at an angle of between about 10 degrees and about 90 degrees, said plurality of third flange members extends radially from said second hinge member at an angle of about 10 degrees, and said plurality of fourth flange members extends radially from said second hinge member at an angle of about 30 degrees.

16. The implantable medical device of claim 13, wherein said first and second flange members comprise a first elongate member having a first geometry and said third and fourth flange members comprises a second elongate member having a second geometry different than said first geometry.

17. The implantable medical device of claim 16, wherein said first elongate member has a first stiffness and said second elongate member has a second stiffness different than said first stiffness.

18. The implantable medical device of claim 13, wherein said barrel portion comprises an elongate member having a first stiffness, said first and second flange portions comprise an elongate member having a second stiffness, and said third and fourth flange portions comprise an elongate member having a third stiffness, wherein each of the first, second, and third stiffnesses are different.

19. The implantable medical device of claim 13, wherein said plurality of first flange members provides a first apposition force, said plurality of second flange members provides a second apposition force, said plurality of third flange members provides a third apposition force, and said plurality of fourth flange members provides a fourth apposition force, wherein each of the first, second, third, and fourth apposition forces are different.

20. An implantable medical device comprising:

a barrel portion comprising a rigid frame having a first end and a second end;

a first flange portion, said first flange portion comprising a plurality of first flange members having a first projecting angle and a plurality of second flange members having a second projecting angle different than the first projecting angle, said plurality of first flange members being discrete and separate from said plurality of second flange members;

a first hinge member formed of a cover material and flexibly coupling said first end of said barrel portion and said first flange portion, said cover material allowing said first flange portion to pivot with respect to said barrel portion;

a second flange portion, said second flange portion comprising a plurality of said first flange members having said first projecting angle and a plurality of said second flange members having said second projecting angle; and a second hinge member formed of said cover material and flexibly coupling said second end of said barrel portion and said second flange portion, said cover material allowing said second flange portion to pivot with respect to said barrel portion; and a plurality of elongate members forming part of the rigid frame of the barrel portion, part of the first flange portion, and part of the second flange portion without the plurality of elongate members extending from the barrel portion through the first hinge member to the first flange portion and from the barrel portion through the second hinge member to the second flange portion.

21. The implantable medical device of claim 20, wherein said first projecting angle is between about 5 degrees and 80 degrees and said second projecting angle is between about 10 degrees and 90 degrees.

22. The implantable medical device of claim 20, wherein said plurality of first flange members has a first length and said plurality of second flange members has a second length, said first length being less than said second length.

23. The implantable medical device of claim 20, wherein said plurality of first flange members comprises a first elongate member having a first geometry and said plurality of second flange members comprises a second elongate member having a second geometry different than the first geometry, wherein said first elongate member has a first stiffness and said second elongate member has a second stiffness different than the first stiffness.

24. The implantable medical device of claim 20, wherein said barrel portion comprises an elongate member having a first stiffness and said first and second flange portions each comprise one or more elongate members having a second stiffness different than the first stiffness.

25. The implantable medical device of claim 20, wherein said first flange portion provides a first apposition force and said second flange portion provides a second apposition force different than said first apposition force, wherein said plurality of first flange members provides a third apposition force and said plurality of second flange members provides a fourth apposition force different than said third apposition force.

* * * * *